United States Patent [19]

Colwell et al.

[11] Patent Number: 4,818,753
[45] Date of Patent: Apr. 4, 1989

[54] SYNTHESIS AND METHOD OF USE FOR 2,4 DIAMINOQUINAZOLINE

[75] Inventors: William T. Colwell, Menlo Park; Joseph I. DeGraw, Sunnyvale, both of Calif.

[73] Assignee: SRI International, Menlo Park, Calif.

[21] Appl. No.: 98,499

[22] Filed: Sep. 18, 1987

[51] Int. Cl.$^4$ .................... A61K 31/505; C07D 239/95
[52] U.S. Cl. .................................. 514/155; 514/156; 514/157; 514/158; 514/260; 544/291
[58] Field of Search ............... 544/291; 514/260, 155, 514/156, 157, 158

[56] References Cited

U.S. PATENT DOCUMENTS 2,945,859  7/1960  Hitchings et al. .................. 544/291
4,677,219  6/1987  Berman et al. ..................... 544/291

OTHER PUBLICATIONS

"Chemical Abstracts", vol. 53, 1959, Col. 123166.
Hitchings, et al., (III), "Chemical Abtracts", vol. 57, 1962, Col. 16633g.
Oakes, et al., "Chemical Abstracts", vol. 58, 1963, Col. 521d.
Modest, et al., "Chemical Abstracts", vol. 63, 1965, Col. 5639f.
Castaldo, R. A., et al., *Antimicrob. Agents and Chemotherapy* 15:81-86 (1979).
DeGraw, J., et al., *J. Med. Chem.* 17:762-764 (1974).
Colwell, W. T., et al., *Chemistry and Biology of Pteridines*, Kisliuk/Brown, eds., Elsevier, North Holland Inc., pp. 215-218 (1979).
Hariri, A. R., et al., *Proc. Soc. Exp. Biol. Med.* 151:173-176 (1976).

*Primary Examiner*—Glennon H. Hollrah
*Assistant Examiner*—James H. Turnipseed
*Attorney, Agent, or Firm*—Ciotti & Murashige, Irell & Manella

[57] ABSTRACT

Compounds of the formula

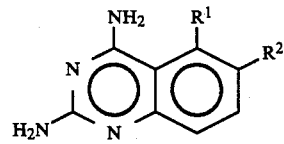

wherein $R^1$ is H, methyl, ethyl, or chloro and $R^2$ is hydrocarbyl of 1-12 C are useful as antifungal agents. Compounds of this series wherein $R^2$ is 7-12 C are novel. A new synthetic method for the compounds is also described.

14 Claims, 1 Drawing Sheet

Synergy Plot of the Activity of the Combination of 2,4-Diamino-5-Methyl-6-Octylquinazoline (C8) Plus Sulfamethoxazole (SMX) vs Candida albicans (10231)

SYNTHESIS AND METHOD OF USE FOR 2, 4 DIAMINOQUINAZOLINE

TECHNICAL FIELD

The invention relates to the fields of synthetic organic methods and antifungal agents. More particularly, the invention relates to new methods for the synthesis of the alkylated 2,4-diaminoquinazolines and to methods using the resulting compounds as antifungal agents.

BACKGROUND ART

The preparation of what were generically described as 2,4-diaminoquinazolines substituted with lower alkyl in the 5 or 6 position was disclosed more than 20 years ago (U.S. Pat. No. 2,945,859, issued July 19, 1960), and a limited number of such compounds were, in fact, prepared. The compounds prepared were described as antibacterial agents, and related compounds were subsequently shown to be bactericidal in an agricultural context (U.S. Pat. No. 3,541,212) and to be hypotensive agents (U.S. Pat. No. 3,663,706). It was later shown that the series of 2,4-diamino-5-methyl-6-alkylquinazolines are effective inhibitors of dihydrofolic reductase isolated from mycobacterium and were effective growth inhibitors for this bacterium. It was also demonstrated that the combination of these compounds with diaminodiphenyl sulfone (DDS) produced a synergistic effect in inhibiting growth of mycobacteria (DeGraw, J., et al, *J Med Chem* (1974) 17: 762–764). A review of this work in comparison with other compounds was published by Colwell, W. T., et al, in "Chemistry and Biology of Pteridines" (1979), Kisliuk/Brown, eds., Elsevier, North Holland Inc., pp 215–218.

More complex compounds of the 2,4-diaminoquinazoline series were studied for their activity against various fungi and yeast by others. Hariri, A. R., et al, *Proc Soc Exp Biol Med* (1976) 151: 173–176 showed that the complex derivative, 2,4-diamino-6-(2-(3,4-dichlorophenyl)acetamido)quinazoline, was active in vitro and in vivo against the encapsulated yeastlike fungus, *Cryptococcus neoformans*. Their work showed that while other quinazoline derivatives were known to have activity against eucaryotic parasites such as the Plasmodium species, this particular compound showed no activity against these parasites. The minimum inhibitory concentration (MIC) of the Hariri quinazoline compound was approximately 6–8 ug/ml with respect to *C. neoformans*.

Additional complex derivatives of 2,4-diaminoquinazoline, which contain either a fused pyrrole ring at the 5, 6-positions or a complex amino sidechain at the 6-position were shown to be active against various Candida species at MIC levels of 0.5–4 ug/ml Castaldo, R. A., et al *Antimicrob Agents and Chemotherapy* (1979) 15: 81–86. This activity was quite variable with respect to a total of 17 candidate isolates; and the compounds in the series showed great difference in levels of activity. Indeed, most of the compounds of the series were not particularly active, and it appeared that the nature of the substituent(s) at the 5 and 6 positions (all of which, furthermore, contained rings) was quite critical. One of the compounds, N-cyclopropylmethyl-5,6-pyrrolo-2,4-diaminoquinazoline, showed synergistic activity against Candida in the presence of sulfamethoxazole (SMX). None of these compounds of the 2,4-diaminoquinazoline series has found clinical use against yeast or fungal infections although there is considerable need for effective antifungals. The commonly used antifungals, ketoconazole and amphotericin B, have unmanageable and serious side effects.

DISCLOSURE OF THE INVENTION

It has now been found that simple members of the 2,4-diaminoquinazoline series are highly effective antifungal agents. They are also synergistic with the sulfa drugs. Because of their effective antifungal activity, aided also by their synergistic effect with sulfa compounds, their low level of toxicity, and their practicality of synthesis, the 2,4-diaminoquinazolines described below are provided in a practical manner for the treatment of yeast and fungal infections.

Accordingly, in one aspect, the invention relates to a method to treat fungal infection by use of the 5 and/or 6 substituted 2,4-diaminoquinazolines described below. In another aspect the invention is directed to an improved method for the synthesis of this series of compounds. In still another aspect, the invention relates to a method of treating yeast infections by coadministration of the above referenced compounds with sulfa drugs. Finally, the invention is also directed to compounds of the formula

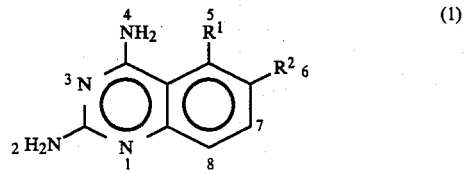

wherein $R^1$ is H, methyl, ethyl or chloro, and $R^2$ is a hydrocarbyl substituent of 7–12 carbons, and the pharmaceutically acceptable acid addition salts thereof.

MODES OF CARRYING OUT THE INVENTION

Figure 1:
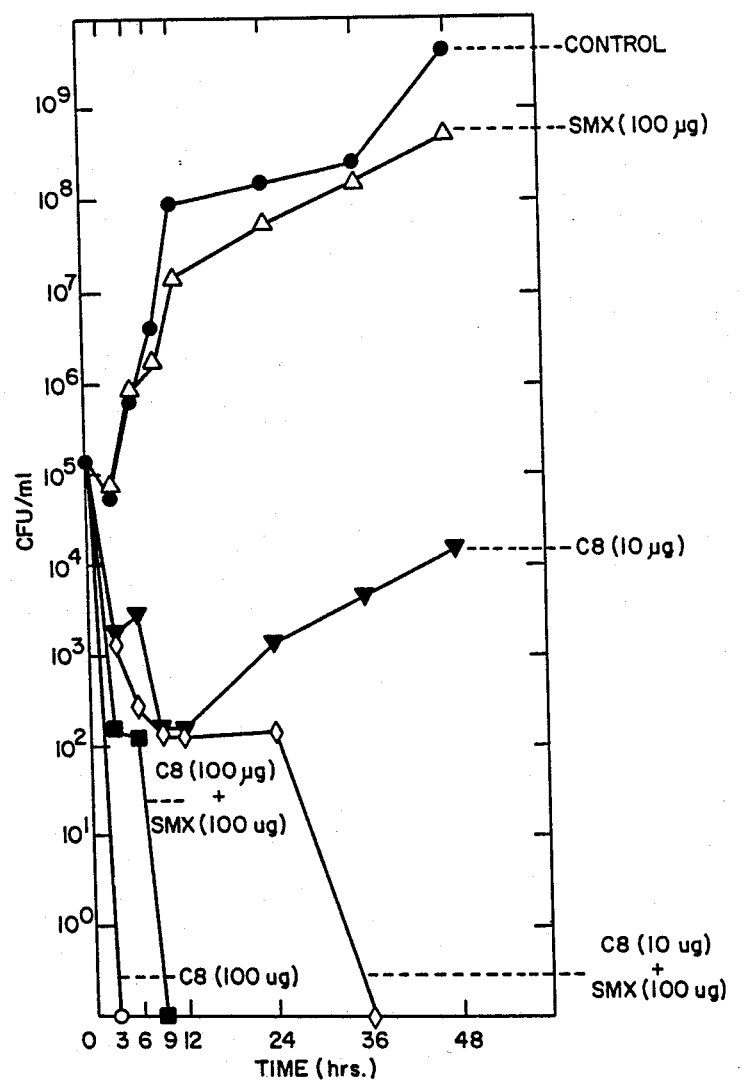
FIG. 1 shows graphical representation of the synergistic effect of a sulfa drug with a compound of the invention.

The 2,4-diaminoquinazoline compounds useful in the method of the invention have the formula

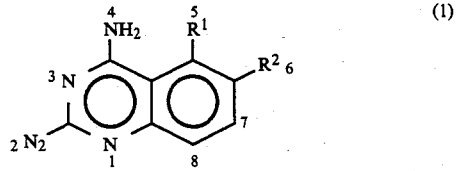

wherein $R^1$ is H, methyl, ethyl, or chloro, preferably H or methyl; and $R^2$ is H or hydrocarbyl of 1–12 carbons, preferably 2–9C. The hydrocarbyl group is a saturated or unsaturated, aliphatic or aromatic, straight or branched chain or cyclic moiety, such as methyl, isopropyl, buten-2-yl, 4 methylpenten-3-yl, hexyl, n-dodecanyl, i-octanyl, 3-methyl hexanyl, n-nonyl, and may include a phenyl moiety such as phenyl ethyl, and the like.

The compounds of the invention can be supplied in free base form, but are preferably supplied as their acid-addition salts. Suitable acid-addition salts include those formed from the inorganic acids such as hydrochloric, hydrobromic, sulfuric, and phosphoric, or those formed from organic acids such as acetic, propionic, pyruvic, succinic, etc. One or both of the amino groups may be thus derivatized.

The compounds of the invention are potent antifungal agents and may also be used in conjunction with sulfa drugs, with which they exhibit a synergistic effect. By sulfa drugs is meant any commonly used antibacterial compound derived from sulfonic or sulfanilic acid. Included among these compounds are, for example, SMX, and sulfanilamide, and diaminodiphenyl sulfone.

SYNTHESIS METHOD

The compounds of the invention are synthesized by the following novel method, shown in reaction scheme 1. The intermediates having various $R^2$ substituents can thus be obtained from the common intermediate

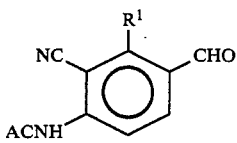
(2)

and the synthesis completed by reaction of the resulting compound of the formula

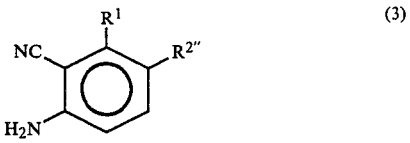
(3)

with

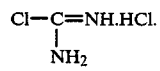

The priming of $R^{2'}$ indicates that this hydrocarbon group may not yet be in its final form.

As shown in Reaction Scheme 1, the initial conversion of the nitroaniline to a benzonitrile (step 1) is conducted by first converting the nitroaniline to the corresponding diazonium salt and mixing the diazonium salt with a solution containing cuprous ion and cyanide ion.

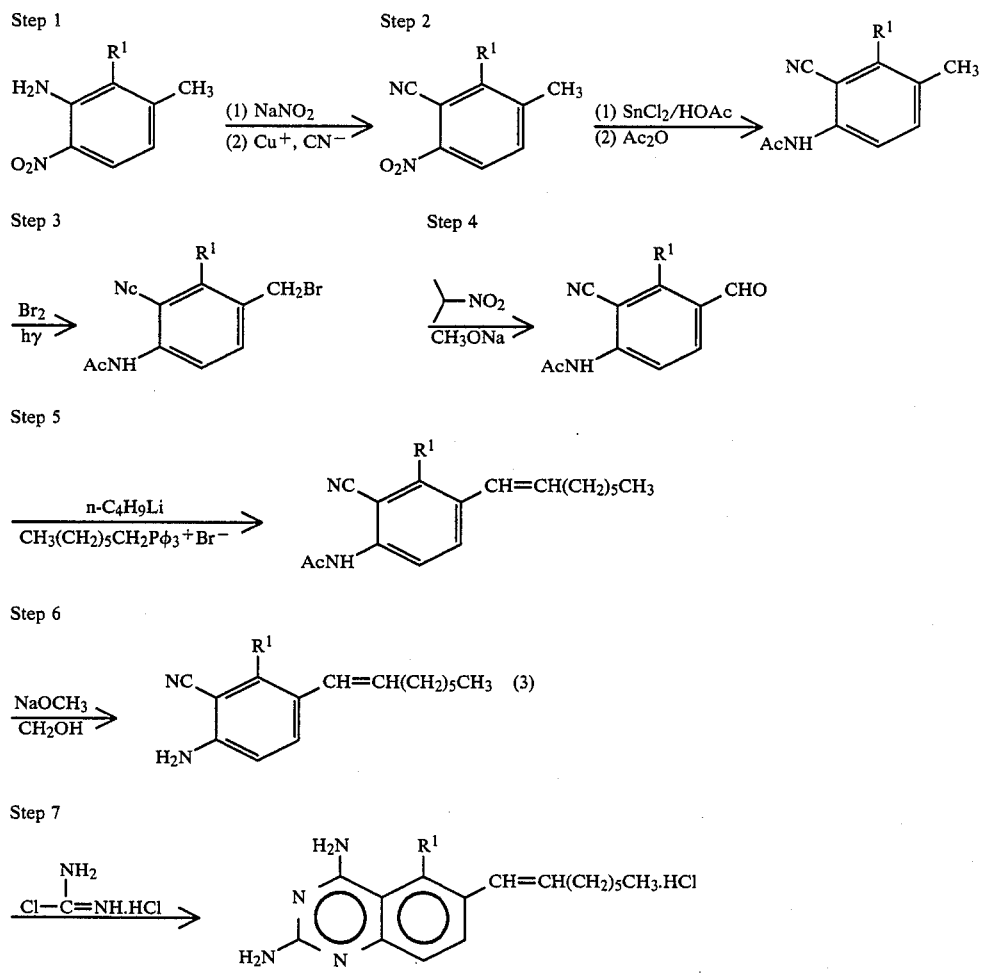

Step 8

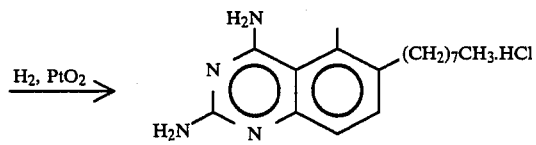

The conditions and relative amounts of reactants are conveniently those described by Fisher, A., et al, *Can J Chem* (1974) 52: 1236, incorporated herein by reference. Reduction of the nitrobenzonitrile to the acetamidobenzo-nitrile (step 2) is conducted by reduction using, for example, stannous chloride or other comparable reducing agent in a suitable polar solvent. If stannous chloride is used as the reducing agent, the solution should be acidic. The reaction is conducted at a convenient temperature, such as about 30°-60° C., which temperature must be maintained using cooling when stannous chloride is used.

The resulting amino compound is worked up using conventional means, such as extraction into a polar organic solvent, and if step 3 is to be conducted, then converted to the acetyl derivative by treatment with acetic anhydride. For the compounds of the invention wherein $R^2$ is H or methyl, step 7 is conducted directly to give the compound of formula (1). If $R^2$ is H, the starting material will be

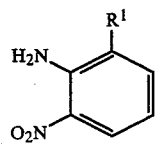

If $R^2$ is not methyl, the methyl group at position 3 is then converted to the bromomethyl derivative by n-bromosuccinimide and azo(bis)isobutyro-nitrile (AIBN) and catalyzed by ultraviolet light in a halogenated solvent. The reaction is conducted under an inert atmosphere at reflux temperatures.

The resulting product is purified using standard techniques, and then converted, in step 4 of the sequence, to the corresponding aldehyde. This conversion is effected by treatment with a suitable alkoxide, especially sodium methoxide, dissolved in the corresponding alkanol in the presence of 2-nitropropane. This reaction is conducted in ambient conditions, and the harvested product, which is the $R^1$-substituted 4-acetamido-3-cyanobenzaldehyde, is recovered using conventional techniques.

This intermediate, of formula (2), is then used for the production of various members of the class of antifungal compounds to which the invention is directed by reaction with suitable reagents to convert the aldehyde substituent to the $R^2$.

The $R^2$ substituent is conveniently added by means of a Wittig reaction using the appropriate alkyl tri-phenylphosphorane, which is prepared from the triphenylphosphonium salt by treatment with a strong base, such as an alkyl lithium, typically n-butyl lithium. The reaction (step 5) is conducted at 0° C. by adding the appropriate phosphorane solution to a solution of the aldehyde of formula (2) in an inert, polar aprotic solvent such as tetrahydrofuran or dimethylformamide. The resulting substituted acetamidobenzonitrile is then converted to the amine by hydrolysis in base (step 6), preferably in the presence of an alkoxide salt in the corresponding alcohol. The resulting free amine of formula (3) is then recovered using standard procedures. The $R^{2'}$ substituent will retain, at this point, unsaturation (a mixture of cis/trans isomers) at the new covalent linkage.

The conversion of the intermediate of formula (3) in step 7 to the corresponding 2,4-diaminoquinazoline is common to most embodiments of $R^2$ (except for methyl or H). In this procedure, the aminobenzonitrile is reacted with chloroformamidine hydrochloride in the presence of a suitable polar solvent at elevated temperatures. After a suitable reaction time, typically 3-10 hours, the mixture is diluted with water and the solid product precipitated and collected. If the unsaturation at positions 1-2 is desired, this is the end of the procedure. However, if a saturated alkyl side chain is preferred, as is typically the case, the resultant of the last step is readily reduced to the saturated form in step 8 by treatment with a suitable reducing agent such as hydrogen or platinum or palladium.

The steps of Reaction Scheme 1, while illustrated in the examples below for $R^1$ as methyl, are also applicable to the other embodiments of $R^1$: H, ethyl, and chloro. These substituents do not interfere with the sequence of reactons.

The compound of the invention wherein $R^2$ contains 7-12 carbons are novel. Also novel are certain intermediates in the synthesis of this general class, as well as the synthetic pathway.

In various aspects of the invention, the invention is directed to conversion of a compound of the formula

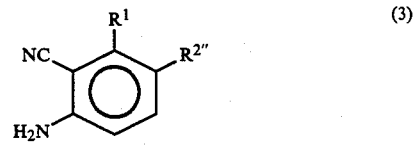

(3)

to a compound of the formula (4):

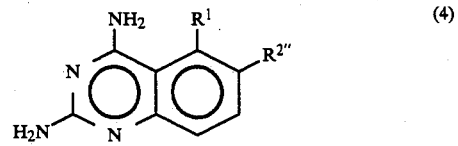

(4)

which comprises treating the compound of formula (3) with chloroformamidine hydrochloride in a polar solvent at elevated temperatures and recovering the compound of formula (4). It is understood that while $R^{2'}$ in the compounds of formulas 3 and 4 is defined in the same manner as that set forth for $R^2$ above, except that it contains unsaturation due to the reaction forming the acetylated form of the compound of formula (3), the desired compound of formula (1) may bear an $R^2$ substituent which differs from that in formula (4). The use of the prime symbol in the compound of formula (4) is intended to signify this.

UTILITY AND ADMINISTRATION

The compounds of the invention are useful as antifungal agents. Accordingly, they may be used to treat fungal infections in animal subjects. The administration of these compounds or their salts may be by any of the accepted modes of administration for antifungal agents, including oral, parenteral, and topical forms.

Depending on the mode of administration intended, the compositions used may be in the form of solid, semisolid, or liquid dosages, and may be supplied as salves, creams, suppositories, pills, capsules, liquids, suspensions, solutions, and the like, preferably in unit dosage forms. The compositions may also be supplied in slow release formulations. The compositions include a conventional pharmaceutical carrier or excipient or slow release regulator and the compound of formula (1) or the pharmaceutically acceptable salts thereof. In addition, the formulas may also include other medicinal agents, pharmaceutical agents, carriers, adjuvants, and the like.

The amount of compound to be administered, of course, depends on the subject being treated, the severity of the infection, and the manner of administration and judgment of the practitioners. However, a suitable effective dose is in the range of 0.5–20 mg/kg/day. Thus, for an average 70 kg human, this would amount to 35–140 mg/day. Suitable pharmaceutical excipients include solid carriers such as lactose, starch, talcum, or sucrose; excipients useful in suppositories such as polyalkylene glycols; or liquids such as water, saline, or buffers. The pharmaceutical composition will contain other auxiliary substances such as wetting or emulsifying agents, and so forth. Methods of preparing suitable dosage forms are known in the art as described in *Remington's Pharmaceutical Sciences*, Mack Publishing Company, Easton, Pa, latest edition.

As the compounds of the invention are believed to function as inhibitors of dihydrofolate reductase, and as it has been demonstrated that they are, indeed, synergistic with antimicrobials known to effect a precursor step to that catalyzed by DHFR, the effectiveness of dosage of the present compounds as antifungals may be enhanced by coadministration with a suitable sulfa drug. Under these circumstances, the dosage levels given above may be lowered, as much as a factor of 10, by use of suitable amounts, conventional in the art, of the various sulfa drug antibiotics.

Thus, as used herein, "effective amount" refers to an amount which is effective under the conditions of administration. When used in combination with another drug, for example, the effective amount may be much less than when used alone—indeed, one component of a mixture may not be effective at all when used alone.

EXAMPLES

The following examples are intended to illustrate, but not to limit, the scope of the invention.

PREPARATION A

Preparation of 2,3-dimethyl-6-nitrobenzonitrile

Solution A: A mixture of 100 g of 2,3-dimethyl-6-nitroaniline and 150 ml of glacial acetic acid at 0° C. was treated with 300 ml of 6M hydrochloric acid. A solution of 50 g of NaNO$_2$ in 150 ml of H$_2$O was then slowly added at 0° C. After the addition of 230 ml of toluene, the mixture was cooled to −20° C. and 322 g of NaHCO$_3$ was added in portions.

Solution B: A solution of 313 g of KCN in 500 ml of H$_2$O was cooled to 0° C. and added to a 0° C. mixture of 120 g cuprous chloride and 300 ml water. The resulting solution was then treated with 500 ml of ethyl acetate.

The diazonium salt mixture (Solution A) was added rapidly to the cuprous cyanide mixture (Solution B) at 0° C. The combined reaction was stirred in additional 1 h at 0° C., then warmed to 20° C. The organic phase was separated and the residue was extracted with ethyl acetate. The combined organic layers were dried and evaporated at reduced pressure. The residue was recrystallized from methyl alcohol to yield 73.9 g (70%) of the title compound, m.p. 107°–108° C.; lit. m.p. 109.5°–110.5° C. Fischer, A., et al, *Can J Chem* (1974) 52: 1236.

EXAMPLE 1

Preparation of 2,3-Dimethyl-6-acetamidobenzonitrile 2,3-Dimethyl-6-nitrobenzonitrile, 22.8 g, was added in portions to a solution of 132 g of stannous chloride in 140 ml of conc. HCl and 140 ml of ethyl alcohol. The temperature was maintained at 40° C. during the addition by application of an ice bath. The reaction was stirred for an additional hour at 40° C. and was poured into an ice cold solution of 700 ml of 6N NaOH. The resulting mixture was adjusted to pH 7, then extracted several times with ethyl acetate. The ethyl acetate extracts were washed with brine, dried, and evaporated at reduced pressure to afford 17.6 g of the crude anilino intermediate. This residue was dissolved in 25 ml of acetic anhydride and stirred overnight at ambient temperature. The solvent was then evaporated and the crude product was recrystallized from ethyl acetate to yield 16.3 g (67%) of crystals, m.p. 125°–126° C.; NMR (CDCl$_3$) 2.30 (6H, s, 3—CH$_3$ and N—COCH$_3$), 2.50 (3H, s, 2-CH$_3$), 7.40 (1H, d, ArH), 8.10 (1H, d, ArH). Anal. Calc'd for C$_{11}$H$_{12}$N$_2$O; C, 70.2; H, 6.43; N, 14.9. Found: C, 70.2; H, 6.44; N, 14.7.

EXAMPLE 2

Preparation of 2-Methyl-3-bromomethyl-6-acetamidobenzonitrile

In a carefully dried Pyrex reaction vessel were combined 10 g of 2,3-dimethyl-6-acetamidobenzonitrile, 300 ml of CCl$_4$, and 200 ml of HCl-free CHCl$_3$ under argon. To this solution was added 10.8 g of N-bromosuccinimide (recrystallized from H$_2$O) and 0.5 g of azo bisisobutyronitrile (AIBN). The reaction was heated to reflux and irradiated with an external General Electric sunlamp. The initially yellow reaction turned red-brown after 1 h when an additional 0.5 g of AIBN was added. After another 2 h, the reaction mixture was poured into H$_2$O, separated, and the aqueous layer reextracted with CHCl$_3$. The combined CHCl$_3$ layers were washed with H$_2$O, saturated NaHCO$_3$ solution, and brine. The dried organic solution was evaporated at reduced pressure and the residue was crystallized from ethyl acetate to yield 6 g (42%) of the title compound, m.p. 152°–153° C. NMR (CDCl$_3$) 2.30 (3H, s, CH$_3$CON), 2.60 (3H, s, CH$_3$), 4.50 (2H, s, —CH$_2$Br), 7.40 (1H, d, ArH), 8.10 (1H, d, ArH), Anal. Calc'd for C$_{11}$H$_{11}$BrN$_2$O: C, 49.5; H, 4.15; N, 10.5. Found: C, 50.3, H, 4.31; N, 10.6.

EXAMPLE 3

Preparation of 4-Acetamido-3-cyano-2-methylbenzaldehyde

To a solution of sodium methoxide, 0.43 g, in 100 ml of methanol, was added 0.84 g of 2-nitropropane. After 15 min, 2 g of 2-methyl-3-bromomethyl-6-acetamidobenzonitrile was added and the resulting solution was stirred for 2.5 h at ambient temperature. The solvent was then evaporated at reduced pressure and the residue dissolved in chloroform. The chloroform solution was filtered, washed with $H_2O$, dried and the solvent removed at reduced pressure. The residue was crystallized from chloroform-carbon tetrachloride to yield 0.8 g (53%) of product, m.p. 170°–173° C. NMR ($CDCl_3$) 2.30 (3H, s, $CH_3CO-N$), 2.90 (3H, s, $CH_3$), 8.00 (1H, d, C—5H), 8.6 (1H, d, C—6H), 10.20 (1H, s, (CHO)d. Anal. calc'd for $CH_{11}H_{10}N_2O_2.\frac{1}{2}H_2O$: C, 63.5; H, 4.84; N, 13.5. Found: C, 63.4; H, 5.00; N, 13.7.

EXAMPLE 4

Preparation of 2-Amino-5-(1-octenyl)-6-methylbenzonitrile

A mixture of 0.165 g of sodium hydride and 15 ml of dry tetrahydrofuran was stirred at 0° C. under argon. 4-acetamido-3-cyano-2-methylbenzaldehyde, 1.0 g, was then added in portions.

A solution of heptyltriphenylphosphorane was separately prepared from the reaction of 2.64 g of the triphenylphosphonium salt and 4.5 ml of 1.6M n-butyl lithium in 15 ml of tetrahydrofuran.

The phosphorane solution was then added dropwise to the aldehyde solution at 0° C. The mixture was warmed to 20° C. and stirred for 1 h. The reaction mixture was then poured into 300 ml of ice-cold 0.1N hydrochloric acid and the resulting mixture was extracted twice with 100 ml portions of ethyl acetate. The EtOAc extract was washed successively with 50 ml portions of water, 5% $NaHCO_3$ and brine. The EtOAc was dried and evaporated in vacuo. The gummy residue was chromatographed on 50 g of silica gel with elution of product by EtOAc/hexane, 1:3, to afford 1.25 g (88%) of solid material containing cis and trans-isomers. Anal. calc'd for $C_{18}H_{24}N_2O$: C, 76.0; H, 8.51; N, 9.85. Found: C, 76.2; H, 8.62; N, 9.96.

A solution of 1.0 g of the acetamido compound in 30 ml of 1% $NaOCH_3$ in $CH_3OH$ was heated at reflux for 18 h. Following neutralization with acetic acid (0.3 ml), the solvent was evaporated and the residue dissolved in 15 ml of dichloromethane. Successive washes were conducted with 15 ml portions of water, 5% $NaHCO_3$, and brine. The organic extract was dried and evaporated to leave 0.82 g (87%) of product as a mixture of cis-trans isomers. Anal. calc'd for $C_{16}H_{22}N_2$: C, 79.3; H, 9.15; N, 11.6. Found: C, 79.4; H, 8.97; N, 11.3.

EXAMPLE 5

Preparation of 2,4-Diamino-5-methyl-6-(1-octenyl)quinazoline

A mixture of 0.64 g of the 2-aminobenzonitrile of Example 4, 0.30 g of chloroformamidine hydrochloride, and 5.0 ml of diglyme was heated at 140°–150° C. for 5 h. The mixture was diluted with 50 ml of water and stirred for 1 h. The precipitated solid was collected by filtration, washed with water and acetone, and dried to leave 0.58 g (78%) of a white solid. (Mixture of cis-trans isomers.) Anal. calc'd for $C_{17}H_{24}N_4.\frac{3}{4}HCl$: C, 66.2; H, 8.05 N, 18.1. Found: C, 66.2, H; 8.05; N, 18.2.

EXAMPLE 6

Reduction to 2,4-Diamino-5-methyl-6-n-octylquinazoline

A mixture of 12.6 g of the olefin mixture of Example 5, 2.0 g of platinum oxide, and 500 ml of methanol was stirred under an atmosphere of hydrogen for 60 h. The catalyst was removed by filtration through a celite pad and the filtrate was evaporated in vacuo. The solid residue was recrystallized from ethanol to afford 10.6 g (83%), m.p. 262°–264° C.; UV (95% EtOH; pH 12). 238 (43,600), 272 (10,900), 347 (5,930); NMR ($CDCl_3$—$CD_3OD$) 0.89 (3H, t, $CH_3CH_2-$), 1.32 (12H, m, $CH_2$), 2.72 (3H, s, 5—$CH_3$), 2.72 (2H, t, Ar—$CH_2$), 7.20 (1H, d, $C_7$—H), 7.47 (1H, d, $C_8$—H). Anal. calc'd for $C_{17}H_{26}N_4.HCl$: C, 63.2; H, 8.43; N, 17.3; Cl, 11.0. Found: C, 63.3; H, 8.46; N, 17.3; Cl, 10.9.

EXAMPLE 7

Additional Antifungal Compounds

Using as starting material the 4-acetamido-3-cyano-2-methylbenzaldehyde prepared in Example 3 and substituting for the procedure in Example 4 the appropriate hydrocarbyltriphenylphosphorane, the following compounds of the invention were prepared:

(a) 2,4-Diamino-5-methyl-6-n-hexylquinazoline; m.p. 170°–172°. UV (EtoH, pH 11) 237 (43,100), 272 (10,900), 347 (5,200). Calc'd for $C_{15}H_{22}N_4.\frac{1}{2}H_2O$: C, 67.4; H, 8.67; N, 21.0. Found: C, 67.5; H, 8.50; N, 20.9.

(b) 2,4-Diamino-5-methyl-6-n-heptylquinazoline; m.p. 167°–169° calc'd for $C_{16}H_{24}N_4.\frac{3}{8}H_2O$: C, 67.6; H, 8.98; N, 19.7. Found: C, 67.9; H, 8.77; N, 19.9. UV (EtOH, pH 11) 237 (43,300), 272 L (11,110), 347 (5,600);

wherein for the intermediate 6-acetamido-3-(1-heptenyl)-2-methylbenzonitrile—[Calc'd $C_{17}H_{22}N_2O$: C, 75.5; H, 8.20; N, 10.4. Found: C, 75.4; H, 8.25; N, 10.3]; for the intermediate 6-amino-3-(1-heptenyl)-2-methylbenzonitrile—Calc'd $C_{15}H_{20}N_2$: C, 78.9; H, 8.83; N, 12.3. Found: C, 79.5; H, 9.16; N, 11.1; for the intermediate 2,4-diamino-5-methyl-6-(1-heptenyl)-quinazoline—Calc'd $C_{16}H_{22}N_4.\frac{1}{2}HCl$: C, 66.6; H, 7.81; N, 19.4. Found: C, 66.5; H, 7.88; N, 19.3.

(c) 2,4-Diamino-5-methyl-6-n-decylquinazoline; m.p. 158°–160° C., Calc'd $C_{19}H_{30}N_4.\frac{1}{4}H_2O$: C, 71.5; H, 9.64; N, 17.6. Found: C, 71.7; H, 9.67; N, 17.4. UV (EtOH, pH 11) 237 (42,000), 272 (9,700), 347 (4,400);

(d) 2,4-Diamino-5-methyl-6-phenethylquinazline, UV (EtOH, pH 11) 238 (41,500); 272 (11,100), 346 (4,300), Calc'd for $C_{17}H_{18}N.\frac{1}{4}HCl$: C, 71.1; H, 6.40; N, 19.5. Found: C, 71.1, H, 6.84; N, 19.1;

with the corresponding intermediates characterized by:

Calc'd for 6-acetamido-3-(2'-styryl)-2-methylbenzonitrile $C_{18}H_{14}N_4O$: Calc'd C, 78.2; H, 5.84; N, 10.1. Found: C, 77.9; H, 5.90; N, 10.0;

Calc'd for 6-amino-3-(2'-styryl)-2-methyl-benzonitrile $C_{16}H_{14}N_2$: Calc'd C, 82.0; H, 6.02; N, 12.0. Found: C, 82.1; H, 6.26; N, 11.8;

Calc'd for 2.4-diamino-5-methyl-6-(2'-styryl)quinazoline $C_{17}H_{16}N_4.\frac{1}{4}HCl$: Calc'd C, 70.8; H, 5.70; N, 19.4. Found: C, 71.0; H, 5.77; N, 19.5.

EXAMPLE 8

Preparation of 2,4-Diamino-6-(1-nonenyl)quinazoline

An intermediate was prepared as follows. A solution of 5,28 g of 2,4-dibenzamido-6-bromomethyl quinazoline and 4.14 g of triphenylphosphine in 200 ml of dimethyl formamide was stirred at 100° C. for 2.5 h. The solvent was evaporated in vacuo and the residue washed with ether. The material was dissolved in $CHCl_3$ and chromatographed on 150 g of silica gel with preelution by $CHCl_3$ followed by $MeOH$—$CHCl_3$, 4:96, to afford 3.6 g (28%) of a tan solid, TLC $R_f$ 0.50 (MeOH—$CHCl_3$, 1:9).

This intermediate was reacted with octanal to obtain the Wittig reaction product as follows. A mixture of 206 mg (4.7 mmoles) of sodium hydride (55% oil suspension) and 50 ml of dimethyl sulfoxide was heated at 75°–80° C. for 1 h. The resulting solution was cooled to room temperature and treated dropwise with a solution of 2.93 g (3.15 mmoles) of the triphenyl phosphine salt (from Step 1) in 10 ml of DMSO. After 10 min, 0.49 ml (3.15 mmoles) of n-octanal was added and the mixture stirred at ambient temperature for 20 h. The dark solution was added to 500 ml of ice water and extracted with three 25-ml portions of $CHCl_3$. The $CHCl_3$ solution was washed with 35 ml of water, dried, and evaporated in vacuo to leave a dark oil. The residue was washed again with water and pentane and dried to leave 676 mg.

The material was dissolved in 120 ml of 0.15M sodium ethoxide in ethanol and the solution heated at reflux for 2 h. The solvent was removed in vacuo and the residue partitioned between 50 ml of $CHCl_3$ and 50 ml of water. The $CHCl_3$ extract was dried and evaporated. The residue was chromatographed on silica gel wwith elution by $MeOH$—$CHCl_3$, 1:4, to afford 240 mg of solid. The material was recrystallized from $CH_3OH$ to give 59 mg of yellow crystals, m.p. 192°–194° C. Anal. calc'd for $C_{17}H_{24}N_4$: C, 71.8; H, 8.51; N, 19.7. Found: C, 71.4; H, 8.59; N, 19.4.

This product was then reduced by dissolving 91 mg of this nonenyl intermediate in 40 ml of ethanol and along with 50 mg of palladium black. The mixture was stirred under an atmoshere of hydrogen for 20 h. The catalyst was removed by filtration and the filtrate evaporated in vacuo. The residue was recrystallized from $CH_3OH$ to yield 53 mg of yellow solid, m.p. 207° C.; ms m/e 286. Anal. calc'd for $C_{17}H_{26}N_4.H_2O$: C, 67.1; H, 9.27; N, 18.4. Found: C, 67.3; H, 8.85; N, 18.7.

EXAMPLE 9

Both broth dilution and agar dilution assays were used to assess the antifungal activity of the compounds of the invention. The cultures were maintained in Sabouraud dextrose broth (SDB) and diluted with DMSO. 2.5 l of SDB was prepared and distributed into sterile vessels as follows: 49 ml into 1 vessel, 27 ml into 3 vessels, 45 ml into 2 vessels.

Five mg/ml concentration of each compound was prepared using DMSO as the solvent; warming and sonication were necessary to dissolve each compound completely. The compounds were then diluted in SDB according to the following protocol:
1. 100 ug/ml—15 mg cmpd+1 ml DMSO+49 ml SDB
2. 30 ug/ml—13 ml (1)+27 ml SDB
3. 10 ug/ml—5 ml (1)+45 ml SDB
4. 3 ug/ml—13 ml (3)+27 ml SDB
5. 1 ug/ml—5 ml (3)+45 ml SDB
6. 0.3 ug/ml—13 ml (5)+27 ml SDB The compound at each concentration in SDB was then dispensed into 6 tubes each containing 4 ml DMSO. Controls (without any compound) were also prepared to insure that the solvent itself was not fungicidal or fungistatic.

Cultures were grown in SDB for 24 h at 30° C. *C. albicans* and *C. neoformans* were diluted 1:10 in SDB before inoculation. Inoculation volume for yeasts was 2 drops of diluted cells per tube. The fungal cultures were homogenized before inoculation. The same volume was added, but without dilution. All tubes were incubated at room temperature on a rotating wheel. After 16 h of incubation at room temperature, the fungistatic assay was set up on agar plates. One hundred ul of broth from tubes which showed no growth were plted out to determine whether the compounds at these levels were fungistatic and/or fungicidal. Yeasts were inoculated onto SDA (the corresponding agar) plates and fungi onto mycosel agar plates. These plates were then incubated at room temperature. The results for twelve compounds of the invention are shown in Tables 1 and 2.

As shown in Table 1, wherein $R^1$ is methyl, the best fungicidal and fungistatic activity is obtained when $R^2$ is n-hexyl, among those compounds tested, including activity against Candida strains. Activity is retained for shorter or longer alkyl substituents, as shown in Table 2.

TABLE 1

($R^1 = CH_3$)
Minimum Inhibitory Concentration (S) or
Minimum Lethal Concentration (C) in ug/ml

| Compound, $R^2$ | | Fungus: | | | | | | |
|---|---|---|---|---|---|---|---|---|
| | | $F_1$ | $F_2$ | $F_3$ | $F_4$ | $F_6$ | $F_{12}$ | $F_{19}$ |
| H | S | >100 | >100 | >100 | >30 | >30 | >30 | >100 |
| | C | >100 | >100 | >100 | >30 | >30 | >30 | >100 |
| —$CH_2CH_2CH_3$ | S | >100 | >100 | >100 | 30 | >30 | >30 | >100 |
| | C | >100 | >100 | >100 | >30 | >30 | >30 | >100 |
| —$CH_2(CH_2)_2CH_3$ | S | 100 | 100 | 30 | 10 | >30 | 30 | 100 |
| | C | >100 | 100 | 30 | 30 | >30 | >30 | >100 |
| —$CH_2CH_2CH(CH_3)_2$ | S | 100 | 100 | 10 | 10 | >30 | 30 | 100 |
| | C | 100 | 100 | 30 | 10 | >30 | >30 | >100 |
| —$CH_2(CH_2)_3CH_3$ | S | 100 | 100 | 10 | 10 | 30 | 30 | 100 |
| | C | 100 | 100 | 30 | 30 | >30 | >30 | 100 |
| —$CH_2(CH_2)_4CH_3$ | S | 30 | 30 | 3 | 3 | 30 | 10 | 100 |
| | C | 30 | 30 | 10 | 3 | >30 | 30 | 100 |
| Tolnaftate | S | >100 | >100 | >100 | ≦0.1 | ≦0.1 | ≦0.1 | ≦0.3 |
| | C | >100 | >100 | >100 | 10 | 3 | 10 | 30 |
| Miconazole | S | 10 | 30 | ≦0.1 | ≦0.1 | 1 | 3 | ≦0.1 |

TABLE 1-continued ($R^1 = CH_3$)
Minimum Inhibitory Concentration (S) or
Minimum Lethal Concentration (C) in ug/ml

| Compound, $R^2$ | | $F_1$ | $F_2$ | $F_3$ | $F_4$ | $F_6$ | $F_{12}$ | $F_{19}$ |
|---|---|---|---|---|---|---|---|---|
| | C | 30 | 30 | 10 | 1 | 30 | 30 | 30 |

1. Sabouraud Dextrose Broth - pH 5.5
$F_1$ *Candida albicans* (10231)
$F_2$ *Candida albicans* (14053)
$F_3$ *Cryptococcus neoformans* (13690)
$F_4$ *Epidermophyton floccosum* (15693)
$F_6$ *Trichophyton mentagrophytes* (11481)
$F_{12}$ *Microsporum gypseum* (14683)
$F_{19}$ *Penicillium citrinum* (9849)
S Fungistatic
C Fungicidal As shown in Table 2, this activity is maintained and improved for the longer chain $R^2$ embodiments, as well.

TABLE 2

| Compound, $R^1,R^2$ | | $F_1$ | $F_3$ | $F_4$ | $F_6$ | $F_{12}$ |
|---|---|---|---|---|---|---|
| $R^1 = H$ | S | 100 | 3 | 30 | >100 | 100 |
| $R^2 = $ | C | >100 | >30 | ≦0.3 | >100 | >100 |
| $CH_2(CH_2)_7CH_3$ | | | | | | |
| $R^1 = CH_3$ | S | 30 | 3 | 30 | 30 | 30 |
| $R^2 = $ | C | >100 | 3 | 30 | 30 | 100 |
| $-CH_2(CH_2)_4CH_3$ | | | | | | |
| $R^1 = CH_3$ | S | 30 | 3 | 10 | 30 | 30 |
| $R^2 = $ | C | >100 | 10 | 30 | 30 | 100 |
| $-CH_2(CH_2)_5CH_3$ | | | | | | |
| $R^1 = CH_3$ | S | 10 | 3 | 1 | 100 | 30 |
| $R^2 = $ | C | 100 | 3 | 30 | 10 | 100 |
| $-CH_2(CH_2)_6CH_3$ | | | | | | |
| $R^1 = CH_3$ | S | 30 | 3 | 30 | >100 | 100 |
| $R^2 = $ | C | >100 | 30 | 10 | 30 | >100 |
| $-CH_2(CH_2)_8CH_3$ | | | | | | |
| $R^1 = CH_3$ | S | 100 | 10 | 30 | 30 | 100 |
| $R^2 = $ | C | >100 | 30 | 100 | 30 | >100 |
| $-CH_2(CH_2)C_6H_5$ | | | | | | |
| Tolnaftate | S | >100 | >100 | ≦0.3 | ≦0.3 | ≦0.3 |
| | C | >100 | >100 | ≦0.3 | >100 | 30 |
| Miconazole | S | 10 | ≦0.3 | ≦0.3 | ≦0.3 | 1 |
| | C | 100 | 10 | ≦0.3 | 10 | 30 |
| DMSO | S | >100 | >100 | >100 | >100 | >100 |
| Control | C | >100 | >100 | >100 | >100 | >100 |

1. Sabouraud Dextrose Broth - pH 5.5
$F_1$ *Candida albicans* (10231)
$F_2$ *Candida albicans* (14053)
$F_3$ *Cryptococcus neoformans* (13690)
$F_4$ *Epidermophyton floccosum* (15693)
$F_6$ *Trichophyton mentagrophytes* (11481)
$F_{12}$ *Microsporum gypseum* (14683)
S Fungistatic
C Fungicidal As shown in Table 2, activity is maintained against all species as $R^2$ increases from C6 to C10.

In addition, FIG. 1 shows the synergistic activity of the compounds of the invention wherein $R^1$ is methyl and $R^2$ is n-octyl with SMX against Candida. As shown in FIG. 1, control cultures and cultures treated with SMX alone (100 ug) increased over a 36-h period to approximately $10^8$ cfu/ml. Cultures treated with 10 ug of 2,4-diamino-5-methyl-6-octyl quinazoline alone increase rapidly, but growth is then diminished so that after 36 h only $10^4$ cfu/ml is obtained. However, when the cultures are treated with a combination of 10 ug of the invention compound and 100 ug SMX, after an initial growth spurt, the cfu/ml is reduced to $10^2$ after 9 h and to zero after 36 h. When 100 ug of each compound is used, there are no cfus after only 9 h.

For the agar dilution assay, the test panel consisted of 18 yeastlike and 3 *Filamentus fungii*. Four media were used. These were yeast nitrogen base dextrose (0.5% agar) (YNBDA); pH 5.5; YNBDA with pH adjusted to pH 7.5; and micrological agar (MA), pH 7.0; and Sabouraud dextrose agar, pH 5.7. The media was manufactured by Difco (Detroit, MI) and prepared according to the manufacturer's instructions.

The test compounds were solubilized in 10% aqueous DMSO; the control drug, Nystatin, was solublized in 10% aqueous DMF. The drugs were serially diluted twofold in sterile water to yield concentrations of 1.28 mg/ml to 0.63 ug/ml. One ml of diluted drug was added to 9 ml of cooled (50° C.) molten agar in plastic petri plates to yield final drug concentrations in the agar ranging from 128 to 0.063 ug/ml. Appropriate solvent and media control plates were prepared as well, and all plates stored in the dark at 4° C. overnight. The yeast cultures, maintained in yeast maltose (YM; Difco), were transferred to fresh YM medium and incubating overnight at 37° C. with shaking at 250 rpm. After incubation each culture was diluted in sterile saline to yield concentrations of $3 \times 10^5$ to $3 \times 10^6$ cfu/ml. Isolates of aspergillis and penicillium were made on potato dextrose agar slants, and spore suspensions were made following vigorous shaking with sterile glass beads. The spore preparation were used as inocula for these fungi.

Each prepared place was inoculated with the 21-member panel using a Denleigh multipoint inoculator (Sussex, England). The inoculator delivers approximately 1 ul to the agar surface, resulting in inoculation of from $3 \times 10^2$ to $3 \times 10^3$ cfu. The plates were incubated at 28° C. for 48 h, and the minimum inhibitory concentrations (MIC) of each drug were recorded as the lower concentration of the drug permitting no growth or growth of less than 3 cfu/spot.

The results of these assays are shown in Table 3 for 2,4-diamino-5-methyl-6-n-octyl quinazoline. As shown in that table, this compound is inhibitory for a large variety of yeast and *Filamentus fungii*. Comparable determinations using the YNBDA agar at pH 5.5 rather than pH 7.5 gave MIC values of 128 or greater for all cultures except for *Candida tropicalis*, wherein the MIC was only 4. Similarly, with respect to an alternate medium, Sabouraud dextrose agar at pH 5.7, as against most cultures, the MIC was greater than 128; however, against broth strains of *Cr. neoformans*, MICs of only 16 ug/ml were obtained, and against *Penicillium italicum*, 64 ug/ml, and against *C. rugosa*, only 2 ug/ml.

TABLE 3

| FUNGUS | | MINIMUM INHIBITORY CONCENTRATION (μg/ml) | | | |
|---|---|---|---|---|---|
| | | YNBDA[1] | SDA | MA | YNBDA[2] |
| Cryptococcus neoformans | MY1051 | 128 | 16 | 4 | 8 |
| Cr. neoformans | MY1146 | 128 | 16 | 4 | 8 |
| Candida albicans | MY1058 | >128 | >128 | 16 | 32 |
| Ca. albicans | MY1055 | >128 | >128 | 32 | 32 |
| Ca. albicans | MY0992 | >128 | >128 | 16 | 16 |
| Ca. albicans | MY1013 | >128 | 128 | 16 | 16 |
| Ca. albicans | MY1029 | >128 | >128 | 32 | 32 |
| Ca. parapsilosis | MY1009 | >128 | >128 | 8 | 16 |
| Ca. parapsilosis | MY1010 | >128 | >128 | 4 | 8 |
| Ca. tropicalis | MY1011 | >128 | 128 | 16 | 16 |
| Ca. tropicalis | MY1012* | 4 | 2 | 2 | 4 |
| Ca. pseudotropicalis | MY1040 | 128 | 128 | 4 | 4 |
| Ca. krusei | MY1020 | >128 | >128 | 8 | 8 |
| Ca. rugosa | MY1022 | >128 | >128 | 64 | 32 |
| Ca. guilliermondii | MY1019 | >128 | >128 | 16 | 16 |
| Ca. stellatoidea | MY1017 | >128 | 128 | 16 | 16 |
| Torulopsis glabrata | MY1059 | >128 | >128 | 16 | 8 |
| Sac. cerevisiae | MY1027 | >128 | 128 | 4 | 4 |
| Aspergillus fumigatus | MY4839 | >128 | >128 | 64 | 32 |
| A. flavus | MF0383 | >128 | >128 | 64 | 16 |
| Penicillium italicum | MF2819 | 128 | 64 | 4 | 8 |

YNBDA[1] Yeast nitrogen base dextrose agar pH 5.5.
SDA Sabouraud dextrose agar pH 5.7.
MA Mycological agar pH 7.0.
YNBDA[2] Yeast nitrogen base dextrose agar pH 7.5.
*Nystatin resistant isolate.

It is apparent from the foregoing results that not only is the compound extremely toxic with regard to a wide variety of fungi, the effect of pH is critical.

We claim:

1. A method to treat fungal infections in animal subjects which comprises administering to a subject in need of such treatment a compound of the formula:

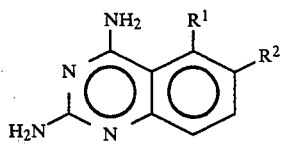

wherein $R^1$ is H, methyl, ethyl, or chloro, and $R^2$ is H or hydrocarbyl (1-12C), or the pharmaceutically acceptable acid-addition salts thereof, in an amount effective as an antifungal agent.

2. The method of claim 1 wherein $R^1$ is H or methyl.
3. The method of claim 1 wherein $R^2$ is hydrocarbyl of 2-9C.
4. The method of claim 1 wherein the compound of formula (1) is 2,4-diamino-5-methyl-6-n-octylquinazoline.
5. The method of claim 1 wherein the compound of formula (1) is 2,4-diamino-5-methyl-6-n-hexylquinazoline.
6. The method of claim 1 wherein the compound of formula (1) is 2,4-diamino-5-methyl-6-n-heptylquinazoline.
7. The method of claim 1 wherein the compound of formula (1) is 2,4-diamino-5-methyl-6-n-decylquinazoline.
8. The method of claim 1 wherein the compound of formula (1) is 2,4-diamino-5-methyl-6-phenylethylquinazoline.
9. The method of claim 1 wherein the compound of formula (1) is 2,4-diamino-6-(1-nonyl)quinazoline.
10. The method of claim 1 wherein the compound of formula (1) is 2,4-diamino-6-n-nonylquinazoline.
11. A method of claim 1 wherein the compound of formula (1) is administered in an effective amount in combination with or in addition to an effective amount of a sulfa drug.
12. A pharmaceutical composition for the treatment of a fungal infection in unit dosage form which contains, as active ingredient, a compound of the formula

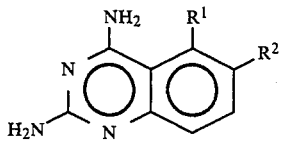

wherein $R^1$ is H, methyl, ethyl, or chloro, and $R^2$ is hydrocarbyl (7-12C), or a pharmaceutically acceptable acid-addition salt thereof, along with a pharmaceutically acceptable excipient.

13. The pharmaceutical composition of claim 12 which further contains as an additional active ingredient a sulfa drug.

14. A compound of the formula

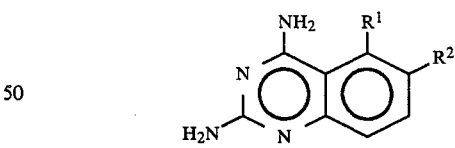

wherein $R^1$ is H, methyl, ethyl, or chloro, and $R^2$ is hydrocarbyl (7-12C).

* * * * *